Figure 1:
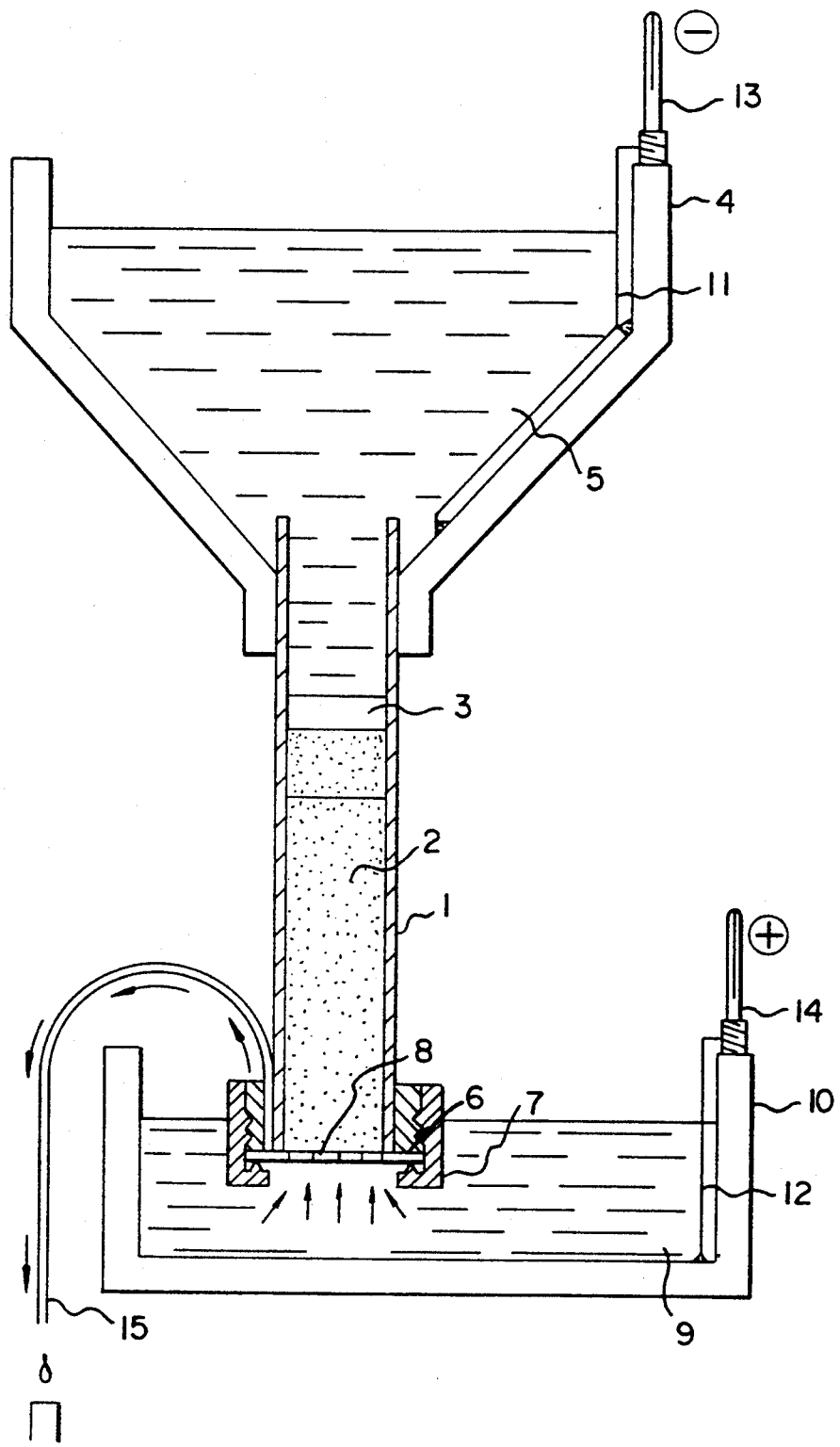

United States Patent

Huynh

[11] Patent Number: 5,151,165
[45] Date of Patent: Sep. 29, 1992

[54] METHODS AND APPARATUSES FOR PREPARATIVE ELECTROPHORESIS

[75] Inventor: Van T. Huynh, Viry Chatillon, France

[73] Assignee: Institut National De La Sante Et De La Recherche Medicale, Paris, France

[21] Appl. No.: 513,029

[22] Filed: Apr. 25, 1990

Related U.S. Application Data

[63] Continuation of Ser. No. 900,158, filed as PCT/FR85/00357, Dec. 10, 1985, abandoned.

[30] Foreign Application Priority Data

Dec. 11, 1984 [FR] France ............................ 84 18910

[51] Int. Cl.⁵ ..................... B01D 61/42; C25D 13/00
[52] U.S. Cl. ............................. 204/299 R; 204/182.8
[58] Field of Search .............. 204/299 R, 182.8, 182.4

[56] References Cited

U.S. PATENT DOCUMENTS 3,697,406 12/1970 Svendsen .
3,704,217 11/1972 Nerenberg .

OTHER PUBLICATIONS

Duesberg et al., "Preparative Zone Electrophoresis of Proteins on Polyacrylamide Gels in 8M Urea", Analytical Biochemistry, vol. 11, pp. 342–361 (1965).

Primary Examiner—John Niebling
Assistant Examiner—Caroline Koestner
Attorney, Agent, or Firm—Larson and Taylor

[57] ABSTRACT

The electrophoresis apparatus of the invention includes a semi-permeable element 6 which makes it possible to take advantage of the phenomenon of electro-endosmosis which is generated during electrophoresis, and outlet tube(s) 15 to transfer the products which emerge from the electrophoresis gel to the exterior by means of a buffer 9 which flows across the semi-permeable element in the direction opposite to that in which the products migrate.

5 Claims, 2 Drawing Sheets

METHODS AND APPARATUSES FOR PREPARATIVE ELECTROPHORESIS

This application is a continuation, of application Ser. No. 06/900,158 filed as PCT/FR85/00357, Dec. 10, 1985, now abandoned.

The subject of the invention is improvements to procedures and apparatuses for preparative electrophoresis.

Gel electrophoresis is known to constitute an efficient separation technique based on the differences in mobility of given substances in an electric field. This technique is widely used to purify substances, in particular, macromolecules such as proteins and nucleic acids.

Its use on a preparative scale presents difficulties, however, on account of the problem associated with the elution of the substances from the gel, which is particularly difficult in the case of macromolecules.

Various solutions have been proposed for the recovery of the substances which have been separated.

For example, one possibility is to cut the gel into slices which are then allowed to swell in a buffer. In this way, the macromolecules diffuse out of the gel into the surrounding buffer. Nonetheless, this technique presents several drawbacks related, in particular, to the slowness of the diffusion process, the consequent dilution of the sample and the low yield.

Another solution depends on the use for the polymerisation of the gel of a monomer which is susceptible to cleavage (for example, bis-acrylylcystamine). After electrophoresis, the gel is sliced and solubilized by another reagent (2-mercaptoethanol in the example cited) in order to release the products. However, it is often found to be necessary to dialyse the solubilized products, a step which frequently leads to adsorption of the products on the dialysis membrane. In addition, the solubilizing agent is not always compatible with some of the substances which have been separated and may thus modify them.

It has also been suggested that the gel or the gel slices be subjected to an electro-elution step at right angles on to hydroxyapatite, and that the separated products be then eluted by changing the buffer.

All of the solutions outlined above lead to the sample being diluted, however, and, in general, a loss of resolution is observed.

Another method consists in continuing the electrophoresis until the products emerge from the bottom of the gel. This lower surface of the gel, which marks the end of electrophoretic migration, and a membrane or porous body form the boundaries of an elution chamber through which a current of buffer flows and carries the products which have emerged from the gel to a fraction collector.

Such elution chambers suffer from a major drawback, in that the products eluted are diluted. In fact, if the rate of flow of buffer is low, the products continue to migrate towards the electrode, they escape from the elution chamber and are lost. If the rate of flow is high enough to prevent this type of loss, then the sample is diluted. The concentration of the sample which is subsequently necessary leads to loss by adsorption to the membrane of the concentrating vessel.

In an attempt to limit the dilution of the sample, a semi-permeable membrane is used in other types of apparatus to form the boundary of the elution chamber. In this case, instead of being lost by continued migration to the electrode, the products are made to adhere to the membrane by the electric current. This, in turn, requires a regulating device which must be able to program the following cycle:

a) the program stops electrophoresis after a certain lapse of time (chosen by the experimenter).

b) in the second step (also chosen by the experimenter), the program reverses the polarity of the electrodes in order to detach the products adhering to the membrane.

c) the program once again stops the electrophoresis and starts a pump which empties the elution chamber into the tubes of a fraction collector.

d) the program then stops the pump and opens an electro-valve, so that the elution chamber is refilled and the cycle may be begun again.

In view of the electronics involved, this type of apparatus suffers from the disadvantage of being expensive.

The aim of the invention is to provide both a procedure for electrophoresis and an apparatus in which this procedure may be carried out which are more satisfactory with regard to the demands made by the technique.

It aims, in particular, to provide an efficient procedure which, after elution and recovery, leads to the desired products in yields at least as high as those obtained by the prior art.

It aims, in addition, to provide an apparatus of simple construction and which can be produced more cheaply than those presently available.

According to the invention, the purification procedure for products of a given sample by gel electrophoresis, with elution of these products by means of a first buffer system, is characterized in that it includes:

the passage of a second buffer in the sense opposite to the direction of migration of the products to be separated and through a semi-permeable element which is fitted tightly and parallel to the lower surface of the gel corresponding to the migration terminus of the products and at a very short distance from that surface, or flush with it. The pores of the semi-permeable element have dimensions of approximately the same order as those of the eluted products.

the removal of the products separated during electrophoresis by the flow of buffer, and the recovery of these products.

It will be noted that these steps entail making use of the phenomenon of electro-endosmosis which occurs during electrophoresis.

In an advantageous manner, the passage of buffer through the semi-permeable element washes the latter continuously and eliminates, at least to a large extent, the loss of the products to be recovered due to adsorption on the semi-permeable element.

The volume of the elution chamber is less than one millimeter and advantageously of the order of 2 or 3 tenths of a millimeter, or even zero, thus making it possible to use only a low rate of flow of buffer and offering the advantage that the purified products are recovered in small elution volumes.

In fact, the volume of the elution chamber in the types of apparatus presently available is greater than one millimeter.

In addition, the use of osmotic flow makes it unnecessary to employ a pump, a factor responsible for the loss of resolution of the apparatus.

According to the procedure most widely used, the sample to be purified is placed on top of a column of gel, the upper part of which is immersed in a buffer contained in a reservoir equipped with an electrode, i.e. the upper electrode buffer, and the lower part of which, together with an elution chamber bounded by a semi-permeable element, is in contact with a buffer contained in a vessel equipped with another electrode, i.e. the lower electrode buffer.

In conformity with the procedure of the invention, the lower electrode buffer flows through the semi-permeable element in the direction opposite to that in which the products migrate.

The upper and lower electrode buffers may be the same or different. The buffer in the gel may also be the same as, or different from, the electrode buffers.

In conformity with standard techniques, the gel may contain several types of buffer, giving rise to different, defined zones in the gel and thus improving the separation of the products.

More especially, the choice of the semi-permeable element (in particular, its nature and porosity), the buffer system (in particular, the nature of the buffer(s) and the difference in their conductivity), the strength of the electric current and the type of gel are all made as a function of the products to be purified and the flow rate one wishes to use to recover the eluate. All of these factors can easily be defined by the specialist.

In particular, the flow rate may vary from 0.05 to 10 ml/h.

As an example, the semi-permeable element may consist of a layer of porous plastic material such as cellulose acetate, polyvinyl chloride or something similar, possibly attached to a support, in particular, paperboard. A membrane of animal skin or a so-called millipore filter may also be used.

The dimensions of the pores may vary widely, it being understood that the pores must be approximately of the same order of magnitude as the products which have migrated and must allow the generation of the phenomenon of electroendosmosis with the buffer as mentioned above. Thus, the membranes referred to as "millipores for dialysis" possess mean diameters of the order of 200 to 300 Å.

In other semi-permeable membranes or layers pore diameters may be of the order of only 10 to 20 Å, or even less.

The gel is composed of an electrically charged polymer. Of the polymers used in electrophoresis, mention may be made of polyacrylamide, agarose, starch, agar or gelose.

An increase of the electric charge of the polymer will intensify the phenomenon of osmosis.

The shape of the gel may be varied. A cylindrical form appears to be the simplest, but gels in the form of a truncated cylinder or a slab may be used.

The buffer may also be chosen from a large range of appropriate systems which include citrate, phosphate, borate or tris buffers, the last-named referring to tris-(hydroxymethyl) aminomethane.

The invention also relates to an apparatus in which the procedure for preparative electrophoresis can be performed.

This apparatus is characterized in that it includes:

a semi-permeable element enabling advantage to be taken of the phenomenon of electro-endosmosis which is generated during electrophoresis, outlets for the removal of the products which emerge from the gel to a collector by means of the buffer flowing across the semi-permeable element in the direction opposite to that in which the products migrate.

The semi-permeable element advantageously meets the requirements set out above.

The outlet tube(s) must be arranged so that all of the molecules of a given type of product which emerge from the gel are removed simultaneously and as quickly as possible.

The lay-out of the outlets through which the eluate is promptly removed and which consist more especially of tubes, depend, in particular, on the dimensions of the gel. For gels of small diameter, these outlets may, however, be arranged alongside the gel, and, for gels of large diameter, they may be placed at the centre of the gel surface. These various arrangements increase the separating power of the apparatus while preventing the remixing of the products which occurs when the removal of molecules of the same type is not effected simultaneously.

According to another design, the electrophoresis apparatus of the invention includes a cooling circuit.

In the case, for example, of an apparatus comprising, as indicated above, a reservoir containing the lower electrode buffer, the height of this reservoir is raised to the level of the bottom of the reservoir containing the upper electrode buffer and the coolant is circulated in a coiled tube installed either in the wall or the interior of the lower reservoir. The coolant cools the buffer which, in turn, cools the column in which electrophoresis is performed. The use of a stirrer, a bar magnet for example, improves heat exchange.

The invention will be illustrated in more detail later by means of the FIGS. 1 and 2 which represent, respectively, embodiments of the invention pertaining to electrophoresis apparatuses.

In FIG. 1, an electrophoresis apparatus is presented which consists of an enclosed space in the form of a cylindrical glass tube 1 containing the gel 2 on which is placed the sample 3 containing the product to be recovered.

The upper part of tube 1 is fitted into the lower part of the funnel-shaped reservoir 4 and is immersed in the upper electrode buffer 5 contained in the reservoir.

The lower end of tube 1 is closed by a semi-permeable membrane 6, screwed tightly to the lower end of tube 1 by a polyethylene collar fitting 7 and forming the lower boundary of an elution chamber of very small volume 8 (its depth is exaggerated in the figure).

The lower part of the tube is immersed in the lower electrode buffer 9 which is contained in the lower reservoir 10.

A cathode 11 and an anode 12 are attached, with their connectors 13 and 14 respectively, to the internal wall of the reservoirs 4 and 10, respectively.

A polyethylene tube 15 is clamped against tube 1 by the screw collar fitting 7 in a manner such that one end of the tube is pressed against the semi-permeable membrane 6 and the other extends outside of the reservoir and is an exit tube to a fraction collector 16.

The bottom of the glass tube 1 is sealed while the gel 2 is polymerised in the usual way. The sample 3 containing the substances to be separated is placed on top of the gel. The substances migrate towards the elution chamber 8 into which the electrode buffer 9 flows after having crossed the semi-permeable membrane 6. The buffer exits via tube 15, thus carrying the products which emerge from the gel to the fraction collector 16.

Figure 2:
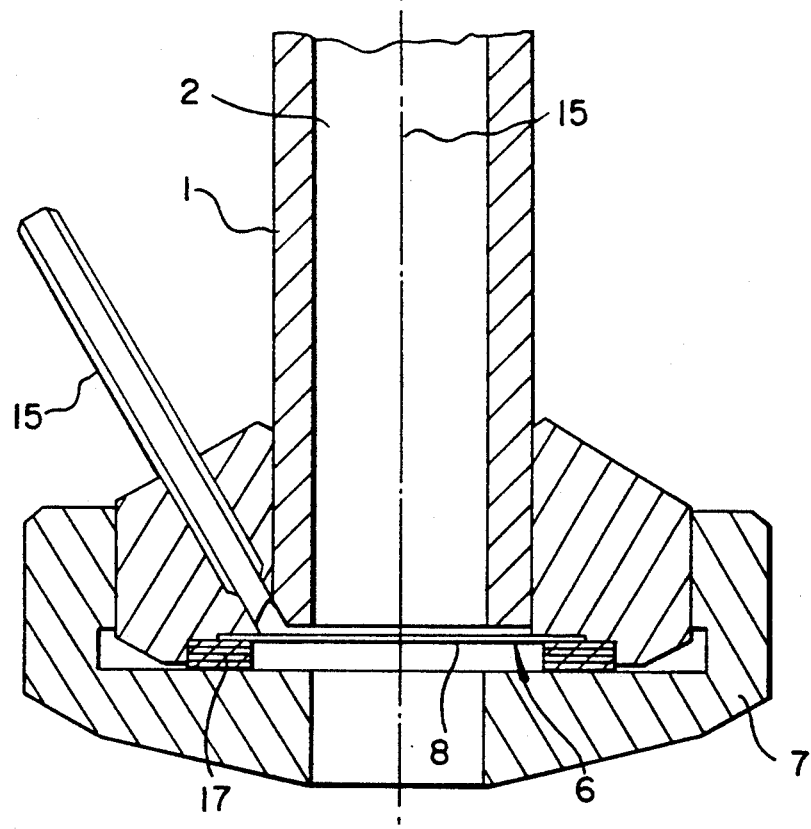

In FIG. 2, another embodiment of the invention of an elution chamber is presented. The same numbers are used to designate the same components as in FIG. 1.

The elution chamber consists of the space between the bottom of the gel 2 and the membrane 6, which latter is maintained tightly against the bottom of the tube and parallel to the gel by means of a screw collar device 7, the tightening of which is mediated by a washer made of a pliable material 18 such as rubber. The eluate is removed by the exit tube 15.

As an example, a description is given of the procedure according to the invention being carried out in the apparatus described above. The example given represents the final step in the purification of a kinase which represents less than 1:10,000 of a mixture containing several hundred proteins.

The whole purification procedure consists of the following steps:
 a) acid precipitation
 b) precipitation by ammonium sulfate
 c) chromatography on DEAE-cellulose
 d) chromatography on phosphocellulose
 e) chromatography on hydroxylapatite
 f) ultracentrifugation in a glycerol gradient
 g) electrophoresis on polyacrylamide gel It will be noted that the contaminants present in the sample used in step g possess charges and masses very similar to those of the enzyme and that, consequently, the contaminants and the enzyme migrate very close to each other (of the order of mm). Nevertheless, some of the fractions of the eluate contain the desired enzyme exclusively.

A polyacrylamide gel of 2 cm$^2$ cross-section is used. The electrode buffers are composed of tris-glycine, pH 8.3 or tris/Bicine (glycine derivative), pH 9.3.

Their conductivity 5 is about 7 mmhos. The gel buffer is composed of tris/HCl, pH 9.8 with a conductivity 5 equal to 0.7 mmhos.

As semi-permeable element, a millipore dialysis membrane is used, the mean pore diameter of which is of the order of 250 Å.

The elution volume for each protein varies from about 0.05 ml to 0.5 ml, depending on the electrophoretic conditions and the amount and migration characteristics of each protein. (It will be recalled that the corresponding elution volumes for a commercially available apparatus lie between 1 and several ml).

50 to 60% of the enzymatic activity is recovered.

It will be noticed that a characteristic of the kinase is that of being partially retained in the gel, a feature which reduces the yield. By labelling the enzyme with a radio-active marker, it can be verified that only a few percent of the radioactivity are adsorbed on to the membrane and that the major loss takes place in the gel.

For other proteins, the yield is at least equal to that obtained with a commercially available apparatus and in the case of hemoglobin, for example, it exceeds 90%.

The invention thus provides a simple and efficient means to purify chemical and biological mixtures by means of preparative electrophoresis by application of the phenomenon of electro-endosmosis to elute the products. Its utilisation for the purification of proteins and nucleic acids is a development of particular importance.

I claim:

1. An apparatus for preparative electrophoresis which does not include a pump consisting essentially of
 a first zone containing an upper electrode and a first electrode buffer system;
 a second zone containing a lower electrode and a second electrode buffer system;
 an enclosed means having upper and lower ends connecting said first and second zones, the upper and lower ends of said enclosed means being immersed in said first and second electrode buffer systems, respectively;
 a continuous separation gel having an upper and lower surface in said enclosed means the upper surface of the gel on which is placed the sample containing the product to be recovered;
 a semi-permeable element having an electroendosmotic capacity maintained tightly and parallel to the lower gel surface;
 an elution chamber defined by the lower surface of said gel and said semi-permeable element;
 at least one outlet for the removal of products which emerge from the gel, without using a pump, by means of the buffer from the second electrode buffer system flowing in the direction opposite to that of the migration of the products to be separated across said semi-permeable element, said outlet being located between the gel and said semi-permeable element, and being with the gel and the molecules to be separated on the same side of the semi-permeable element, the gel and said semi-permeable element being separated by less than one millimeter.

2. Apparatus according to claim 1, characterized in that at least one outlet is used and is arranged alongside the gel or at the center of the gel surface in such a way that all of the molecules of a given type of product which emerge from the gel are removed at the same time and as quickly as possible.

3. Use of an apparatus according to claim 1, for the purification of a chemical or biological composition.

4. Use of an apparatus according to claim 1 for the purification of proteins.

5. The use according to claim 4 wherein the proteins are selected from the group comprising enzymes and nucleic acids.

* * * * *